United States Patent
Levatter

(10) Patent No.: US 11,471,695 B2
(45) Date of Patent: Oct. 18, 2022

(54) DEVICE FOR TARGETED TREATMENT OF DERMATOSES

(71) Applicant: STRATA SKIN SCIENCES, INC., Horsham, PA (US)

(72) Inventor: Jeffrey I. Levatter, Rancho Santa Fe, CA (US)

(73) Assignee: STRATA SKIN SCIENCES, INC., Horsham, PA (US)

(*) Notice: Subject to any disclaimer, the term of this patent is extended or adjusted under 35 U.S.C. 154(b) by 1 day.

(21) Appl. No.: 14/815,424

(22) Filed: Jul. 31, 2015

(65) Prior Publication Data

US 2016/0158575 A1 Jun. 9, 2016

Related U.S. Application Data

(63) Continuation of application No. PCT/US2015/042926, filed on Jul. 30, 2015.
(Continued)

(51) Int. Cl.
*A61N 5/06* (2006.01)
*A61N 5/067* (2006.01)

(52) U.S. Cl.
CPC ............ *A61N 5/0616* (2013.01); *A61N 5/067* (2021.08); *A61N 2005/0627* (2013.01);
(Continued)

(58) Field of Classification Search
CPC .......... A61N 5/0616; A61N 2005/0664; A61N 2005/0658; A61N 2005/0627;
(Continued)

(56) References Cited

U.S. PATENT DOCUMENTS

2003/0228476 A1\* 12/2003 Buhay ............... B32B 17/10036
428/469
2004/0158300 A1\* 8/2004 Gardiner .............. A61N 5/0619
607/88
(Continued)

FOREIGN PATENT DOCUMENTS

CN 2719223 Y \* 8/2005
CN 2719223 Y 8/2005
(Continued)

OTHER PUBLICATIONS

Jaksi et al., "Silver-silica transparent metal structures as bandpass filters for the ultraviolet range", 2005, Journal of Optics A: Pure and Applied Optics, vol. 7, pp. 51-55.\*
(Continued)

*Primary Examiner* — Jonathan T Kuo
*Assistant Examiner* — Vynn V Huh
(74) *Attorney, Agent, or Firm* — Gottlieb, Rackman & Reisman, PC

(57) ABSTRACT

A device that is connectable to a phototherapy apparatus for applying targeted phototherapy to an area of skin to place a skin condition into remission and a method of determining a maximum tolerable dose of phototherapy applied to a treatment area to determine an optimum therapeutic dose to quickly place a skin condition into remission. The dosimetry device can include a housing and an optical matrix arranged within the housing. The optical matrix includes a plurality of at least one of absorptive, reflective and/or partially transmissive regions that each permits a different percentage of light to be delivered to an individual's skin. An assessment can then be made as to the maximum tolerable dose of phototherapy that can be applied to the individual's skin in order to place a skin condition into remission.

13 Claims, 8 Drawing Sheets

Related U.S. Application Data

(60) Provisional application No. 62/137,086, filed on Mar. 23, 2015, provisional application No. 62/031,674, filed on Jul. 31, 2014.

(52) U.S. Cl.
CPC ............... *A61N 2005/0628* (2013.01); *A61N 2005/0644* (2013.01); *A61N 2005/0661* (2013.01)

(58) Field of Classification Search
CPC .... A61N 2005/0628; A61N 2005/0644; A61N 2005/0661; A61N 2005/067; A61N 5/06–2005/073; G02B 5/208; G02B 5/201; G02B 5/22; G02B 5/226; G02B 5/223; G02B 2005/1804; G02B 5/1838; G02B 5/0278; A61B 18/20–18/28
USPC ....................................................... 607/78–92
See application file for complete search history.

(56) References Cited

U.S. PATENT DOCUMENTS

| | | | | |
|---|---|---|---|---|
| 2005/0063045 A1* | 3/2005 | Sakakibara | ............... | G01J 1/08 |
| | | | | 359/361 |
| 2006/0195166 A1* | 8/2006 | Minamoto | ............. | A61B 5/445 |
| | | | | 607/94 |
| 2006/0247609 A1* | 11/2006 | Mirkov | ............... | A61B 18/18 |
| | | | | 606/9 |
| 2007/0016074 A1* | 1/2007 | Abreu | ............... | A61B 6/00 |
| | | | | 600/475 |
| 2009/0160341 A1 | 6/2009 | Justel et al. | | |
| 2013/0018442 A1* | 1/2013 | Irwin | ............... | A61N 5/0616 |
| | | | | 607/94 |

FOREIGN PATENT DOCUMENTS

| | | | |
|---|---|---|---|
| CN | 201230877 Y | * | 5/2009 |
| CN | 201230877 Y | * | 5/2009 |
| CN | 201230877 Y | | 5/2009 |
| CN | 202151357 U | * | 2/2012 |
| CN | 202151357 U | | 2/2012 |
| WO | 2005007003 | | 1/2005 |
| WO | 2016019151 | | 2/2016 |

OTHER PUBLICATIONS

International Search Report and Written Opinion, US Patent and Trademark Office, Application No. PCT/US2015/042926, dated Oct. 26, 2015.

Supplementary European Search Report for co-pending European Patent Application No. 15827333 dated Feb. 6, 2018.

\* cited by examiner

DEVICE FOR TARGETED TREATMENT OF DERMATOSES

CROSS-REFERENCE TO RELATED APPLICATIONS

This patent application is a continuation of PCT/US2015/042926 filed Jul. 30, 2015 which claims benefit under 35 U.S.C. § 119 to U.S. Provisional Patent Application No. 62/031,674, filed Jul. 31, 2014 and U.S. Provisional Patent Application No. 62/137,086, filed Mar. 23, 2015, which are hereby incorporated by reference as part of the present disclosure.

FIELD OF THE INVENTION

The present invention relates to targeted phototherapy treatment of skin conditions and more particularly to a device that dispenses a dose of light into a plurality of dosages of varying intensity levels (energy/unit area) of light that contact an individual's skin to determine an optimum therapeutic dose of phototherapy that can be administered to the individual to aid in the treatment of a skin condition.

BACKGROUND OF THE INVENTION

Methods and apparatuses for targeted phototherapy (e.g., narrow-band, 308 nm excimer lasers dispensing ultraviolet light energy are known as an effective and safe treatment for various dermatoses (e.g., psoriasis, vitiligo, leukoderma, atopic dermatitis, and alopecia areata).

Psoriasis, vitiligo and other skin conditions affect millions of people. These dermatoses can range from mild to severe and can lead to substantial morbidity, psychological stress and can have a profound negative impact on the quality of life of an individual suffering from a skin condition. Although available therapies can reduce the extent and severity of these diseases and improve an individual's quality of life, reports have indicated dissatisfaction with the effectiveness, cost, and inconvenience of current treatment modalities.

A common treatment modality for individuals with psoriasis or vitiligo is to receive phototherapy administered at phototherapy centers. At these centers, individuals are exposed to narrowband (NB) or broadband (BB), UVB light (290-320 nm), or a therapy of psoralen plus ultraviolet light (320-400 nm) within an A range (PUVA). Ultraviolet light reduces the symptoms of psoriasis through immunomodulatory mechanisms. The treatment of atopic dermatitis and alopecia areata with UV light has also been studied, but not to the same degree. Treatment for leukoderma and vitiligo rely on UV light to help re-pigment the skin due to a lack of melanin/melanocytes.

With conventional UVB phototherapy, dosing is predicated on either an individual's Fitzpatrick Skin Type (i.e., skin color and darkness) in conjunction with the thickness of the psoriatic plaque or on a measurement of an individual's minimum erythemal dose (MED). An individual's minimum erythemal dose is the dose of UVB that generates a significant red erythemal skin response in normal/healthy tissue. Dosing higher than an individual's minimum erythemal dose tolerance level can result in undesirable (i.e., more severe) tissue reactions, and even blistering. However, neither of these two methods of determining an individual's appropriate dosing protocol is therapeutically optimal and typically results in dosing at levels that are far too conservative which in turn results in a reduced therapeutic benefit. This is because using the Fitzpatrick Skin Type is merely a guess at an individual's maximum tolerable dose (MTD) (based on historical norms that do not apply to many individuals) and the fundamental limitations of the minimum erythemal dose method that only measures the tolerance of the healthy/normal tissue, not the diseased tissue being treated. In either case, many individuals are regularly administered sub-optimal UVB dosing when clinicians, recognizing that current dosing paradigms are only a crude guess, initiate dosing at even lower levels than might be expected. They do so to avoid unintentional dosing at higher levels than the minimum erythemal dose that might be above an individual's minimal blistering dose (MBD) leading to extreme erythema, blistering, and possible injury. This problem is enhanced by the fact that the optimum dose (i.e., MTD, a dose that is near, but just lower than the MBD) can vary greatly for each individual, making it very difficult, if not impossible, to correctly gauge an individual's optimal dose. As such, the lack of having an objective means of determining an individual's minimal blistering dose prevents clinicians from dosing more effectively at an individual's optimum dose level, which could significantly lower the total number of required UVB treatment sessions to obtain the desired clinical outcome.

As a result of the typically high number of treatment sessions required, the use of phototherapy is commonly limited due to the overall inconvenience of the therapy. Poor compliance with the necessary regimen of regular treatment sessions is common because of the time, travel and the cost, in many cases, to effectively treat the disease. Other less effective therapies (e.g., topical prescriptions and over-the-counter topical creams) are often an individual's more convenient fallback option.

SUMMARY OF THE INVENTION

The present invention is directed to a dosimetry device that aids in determining an individual's optimum dose of phototherapy to aid in the treatment of a skin condition by quickly and easily measuring the individual's phototherapeutic tolerance by assessing the individual's minimum blistering dose in order to then treat a skin condition at or near the individual's maximum tolerable dose. By treating a skin condition at or near an individual's maximum tolerable dose, the overall number of treatment sessions required to place an individual's skin condition into remission can be greatly reduced.

In an embodiment, the present invention is directed to a dosimetry device that is connectable to a phototherapy apparatus for applying targeted phototherapy to a treatment area (e.g., on skin tissue). The device comprises a housing and an optical matrix arranged within the housing that includes a plurality of at least one of absorptive, reflective and/or partially transmissive regions, which each permit a different intensity of light (expressed as percentages of an incident of a light beam) and/or range of light to pass therethrough. In an embodiment, the light that is dispensed from a phototherapy apparatus is UVB light.

In an embodiment, the optical matrix can be connected to the housing. In an embodiment, the optical matrix can be formed within the housing. In an embodiment, the optical matrix can include at most nine regions. In an embodiment, the optical matrix can include five regions. In an embodiment, the intensity of light passing through the regions can range from about 20% in one region up to about 100% in another region. In an embodiment, the intensity of light passing through the regions ranges from about 0% in one region up to about 90% in another region.

In an embodiment, the optical matrix is substantially square and can be about 2 cm by 2 cm with each region sized to be approximately about 5 mm by 5 mm. In an embodiment, each of the regions of the optical matrix are square, rectangular, circular, or ovoid. In an embodiment, the optical matrix can be comprised of a plurality of UVB reflective coatings. In an embodiment, the reflective coatings are configured for an output UVB light of about 308 nm. In an embodiment, each of the regions of the optical matrix includes at least one metallic or a dielectric coating. In an embodiment, each of the regions of the optical matrix includes a different filter.

In an embodiment, the present invention is directed to a method of analyzing a maximum tolerable dose of phototherapy that is capable of being applied to skin tissue to aid in the treatment of a skin condition. The method comprises the steps of providing a dosimetry apparatus that comprises a housing and an optical matrix arranged within the housing that includes a plurality of at least one of absorptive, reflective and/or partially transmitting regions to permit varying transmissions of light to pass therethrough, connecting the dosimetry apparatus to a phototherapy apparatus that is configured to disperse UVB light, arranging the phototherapy apparatus at or near the treatment area and transmitting the UVB light from the phototherapy apparatus and through the regions of the optical matrix such that varying doses of the UVB light will be applied simultaneously or sequentially to the various areas under treatment.

In an embodiment, the method further comprises the step of analyzing the treatment area subsequent to applying the UVB light to the treatment area, for example, approximately 24 to 48 hours after the UVB light is applied thereto, to assess the minimum blistering dose of the skin being treated. In an embodiment, the method can further comprise the step of applying a maximum tolerable dose of the UVB light to the treatment area thereby allowing the application of the optimum therapeutic dose without blistering the treated area.

DETAILED DESCRIPTION OF EMBODIMENTS OF THE INVENTION

Figure 1A:
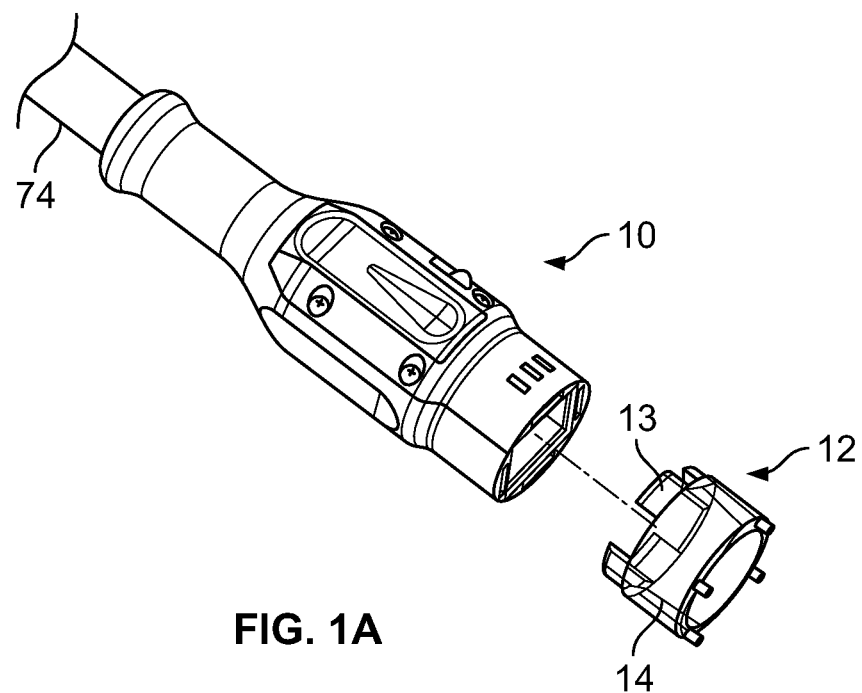
FIG. 1A is a perspective view a hand-held phototherapy delivery apparatus and an end piece that is connectable to the delivery apparatus.
Figure 1B:
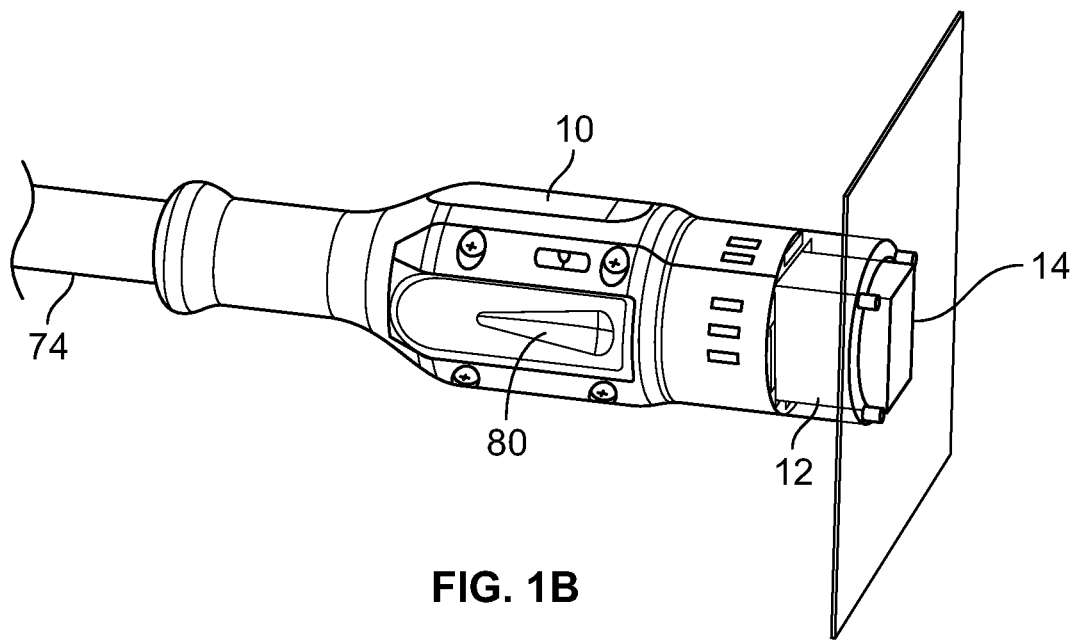
FIG. 1B is a perspective view the hand-held phototherapy delivery apparatus and end piece of FIG. 1A with the end piece attached to the delivery apparatus and a beam of light extending through the end piece.
Figure 1C:
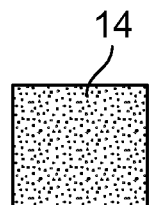
FIG. 1C is an end view of the beam of light extending through the end piece of FIG. 1B.

With reference now to the drawings, FIG. 1A through FIG. 1C illustrate an embodiment of a delivery apparatus 10 and an tip 12 that is connectable thereto to deliver a beam of light 14 that is dispensable from the delivery apparatus 12 into a desired shape so as to apply targeted phototherapy as a treatment modality onto the skin of an individual suffering from a skin condition. As shown in FIG. 1A, the tip piece 12 includes a plurality of tabs 13 that extend from one end of the tip piece 12 in a first direction and that are configured to releasably connect the tip piece 12 to the laser delivery apparatus 10.

As shown in FIGS. 1B and 1C, in an embodiment, the tip piece 12 can size and dispense a square beam 14 of light from the delivery apparatus 10 that can be, for example, 2 cm by 2 cm. An end view of such a square beam 14 of light is illustrated in FIG. 3C.

Figure 2:
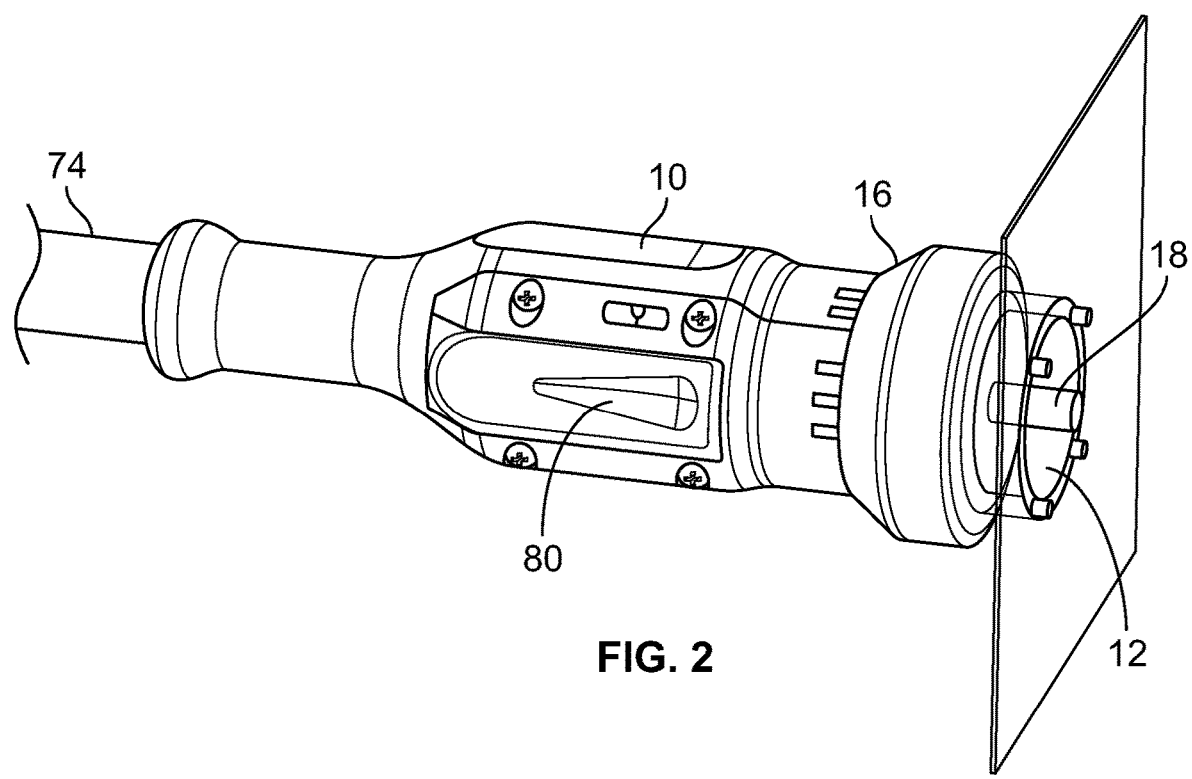
FIG. 2 is a perspective view the hand-held phototherapy delivery apparatus and an embodiment of an end piece with a circular diaphragm connected thereto for beam shaping.

As depicted in an embodiment in FIG. 2, the hand-held phototherapy delivery apparatus 10 and the tip piece 12 can include a diaphragm 16 that partially encompasses the delivery apparatus 10 and the end piece 12 to aid in shaping a beam of light 18. Here, the beam of light 18 is cylindrical.

Figure 3A:
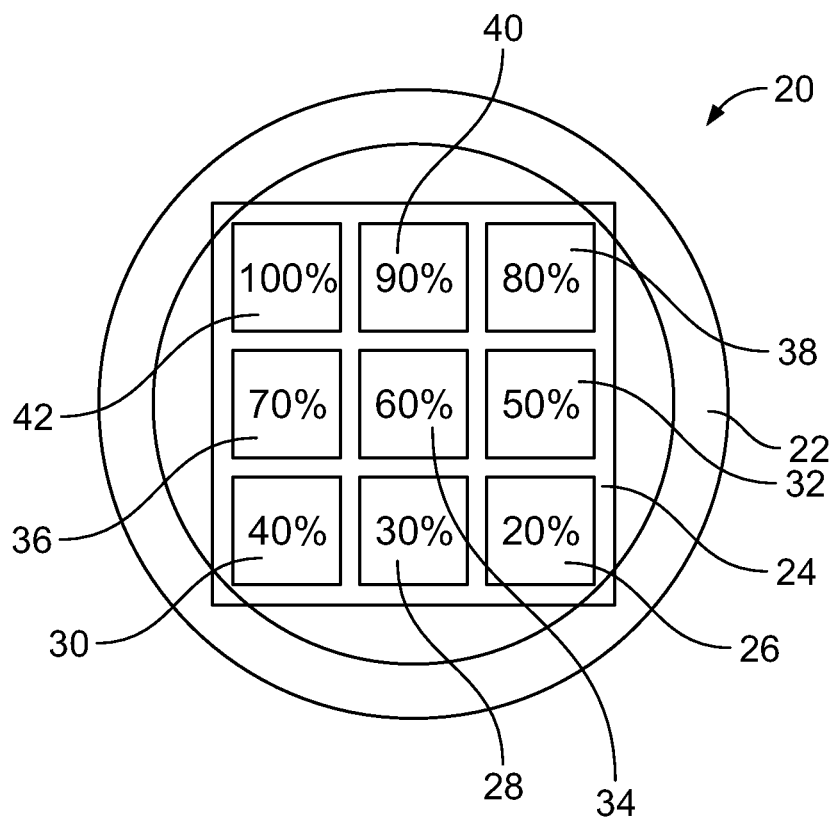
FIG. 3A is a front view of an embodiment of the dosimetry device of the present invention illustrating an embodiment of the photosensitivity matrix.

As illustrated in FIG. 3A, the present invention is directed to a dosimetry device 20 that can distribute a dose of light energy into a plurality of doses of varying levels of light energy that can then be applied onto a treatment area simultaneously or sequentially, to determine an optimum therapeutic dose of phototherapy for an individual suffering from a skin condition by measuring the individual's minimum blistering dose of phototherapy. By treating an individual suffering from a skin condition at or near their minimum blistering dose, the overall number of treatment sessions required to place the individual's diseased skin into remission can be greatly reduced while burning of the individual's skin can be substantially reduced and in most instances avoided. In turn, an individual will be much more likely to be seek out necessary continued treatment of a skin condition due to time and cost savings from known treatment procedures and the lower risk of significant discomfort from blistering than known treatment procedures.

As shown in an embodiment in FIG. 3A, the dosimetry device 20 includes a housing 22 that is configured to be releasably connected the phototherapy delivery apparatus 10 with a sensitivity matrix 24 arranged within the housing 22. As shown in embodiments in FIG. 3A through FIG. 5, the housing 22 of the device 20 is cylindrical. However, the shape of the housing 22 can be any shape, including, but not limited to, square, rectangular, elliptical, triangular, and trapezoidal. The sensitivity matrix 24 can be connected to the housing 22 in any known manner.

Figure 3B:
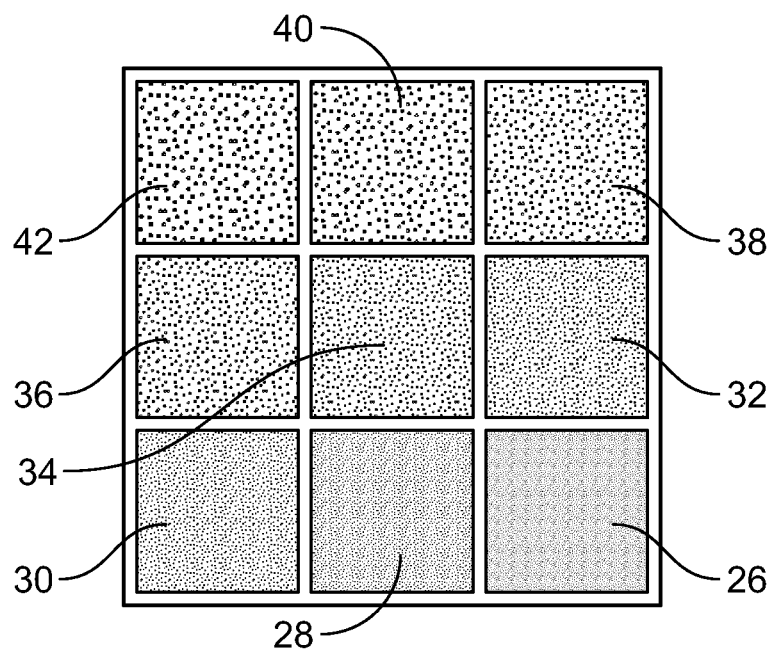
FIG. 3B is an end view of the matrix of FIG. 3A.

In an embodiment in FIGS. 3A and 3B, the sensitivity matrix 24 is comprised of a plurality of regions 26, 28, 30, 32, 34, 36, 38, 40, 42 that are each designated to allow a prescribed intensity of light to pass therethrough to assess an individual's minimum blistering dose tolerance and in turn optimally treat a patient at their maximum tolerable dose. The sensitivity matrix 24 includes nine regions 26, 28, 30, 32, 34, 36, 38, 40, 42 that form a three by three matrix. However, the number of regions and arrangement can vary and the matrix 24 can be comprised of any number of regions that can be arranged in any desired matrix or pattern to change what would have otherwise been a single unique dose level into an array of multiple dose levels simultaneously covering the entire range of potentially applicable therapeutic treatment levels.

In an embodiment, the regions 26, 28, 30, 32, 34, 36, 38, 40, 42 of the sensitivity matrix 24 are comprised of absorptive and/or reflective material that allows for varying intensities of light to pass therethrough. In another embodiment, the regions 26, 28, 30, 32, 34, 36, 38, 40, 42 of the sensitivity matrix 24 are each comprised of partially transmissive material or filters that allows for varying intensities of light to pass therethrough. In an embodiment, the matrix 24 is comprised of fused silica optical components. In an embodiment, the regions 26, 28, 30, 32, 34, 36, 38, 40, 42 of the matrix 24 can be comprised of totally and/or partially reflective materials. The reflective materials can be a dielectric interference filter (e.g., partial reflector). In an embodiment, the filter can be a multi-dielectric interference filter. In an embodiment, the filter can be a metallic coating, including a dielectric enhanced metallic reflector. In an embodiment, the filter can be metallic and comprised of materials such as aluminum or silver. In an embodiment, the filter can be a combination of dielectric interference filter, a multi-dielectric interference filter and a metallic coating.

In an embodiment, the filters reflect a fraction of a dose of energy between about 0% and 99% and segment the dose into multiple beams or streams of energy of varying intensities and transmit the multiple beams or streams of energy of varying intensities onto an individual.

In an embodiment, the intensity of light that is able to pass through the regions 26, 28, 30, 32, 34, 36, 38, 40, 42 of the matrix 24 shown in FIGS. 3A and 3B can range from approximately about 20% to 100%. In another embodiment, intensity of light that is able to pass through the regions 26, 28, 30, 32, 34, 36, 38, 40, 42 of the matrix 24 can range from approximately about 20% to 90%. However, the number, shape and intensity of light being permissible to pass through the region 26, 28, 30, 32, 34, 36, 38, 40, 42 of the matrix 24 can vary and be greater or small than the numbers described herein.

Figure 4:
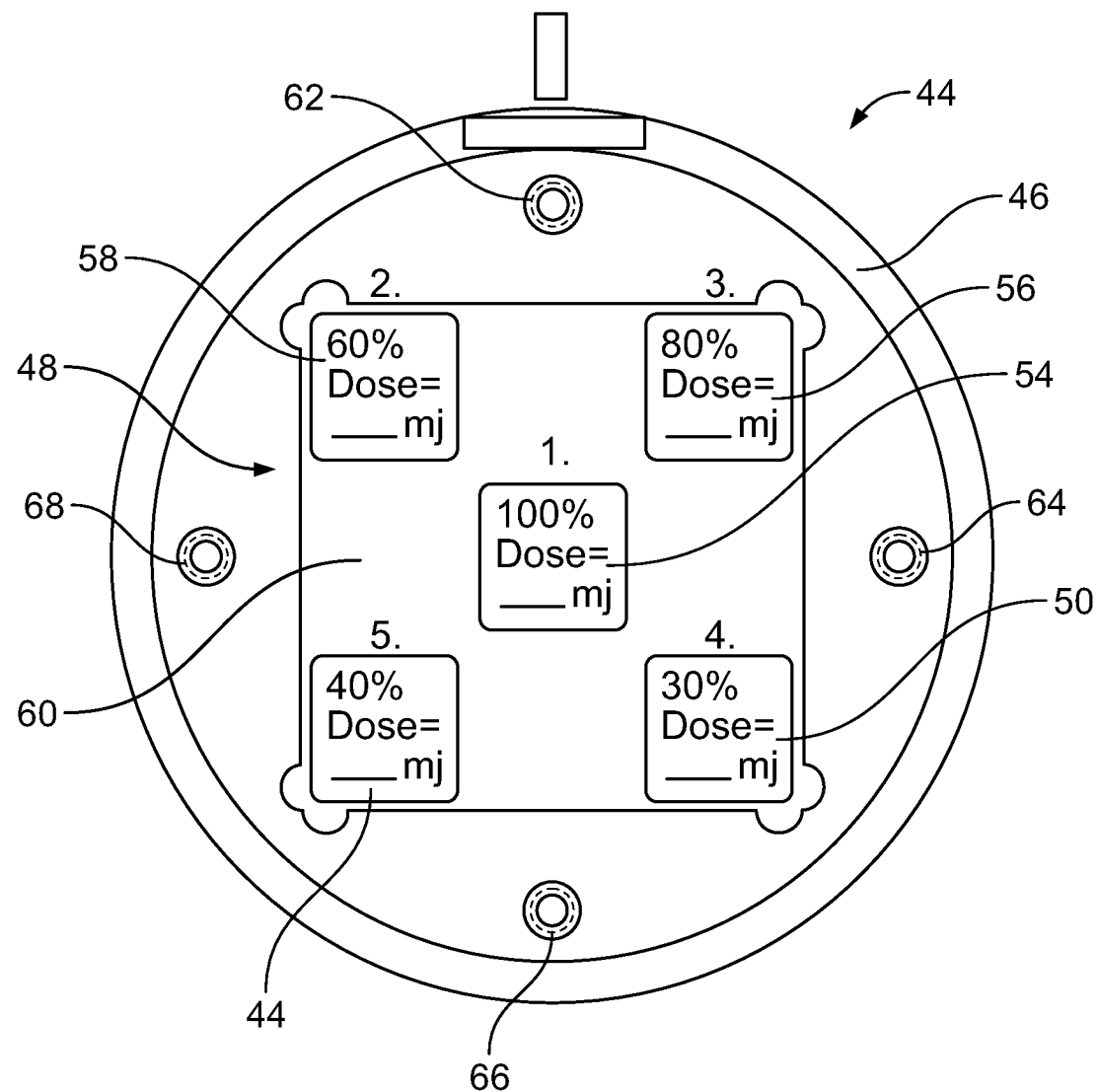
FIG. 4 is an end view of an embodiment of a dosimetry device of the present invention illustrating an embodiment of a photosensitivity matrix.
Figure 5:
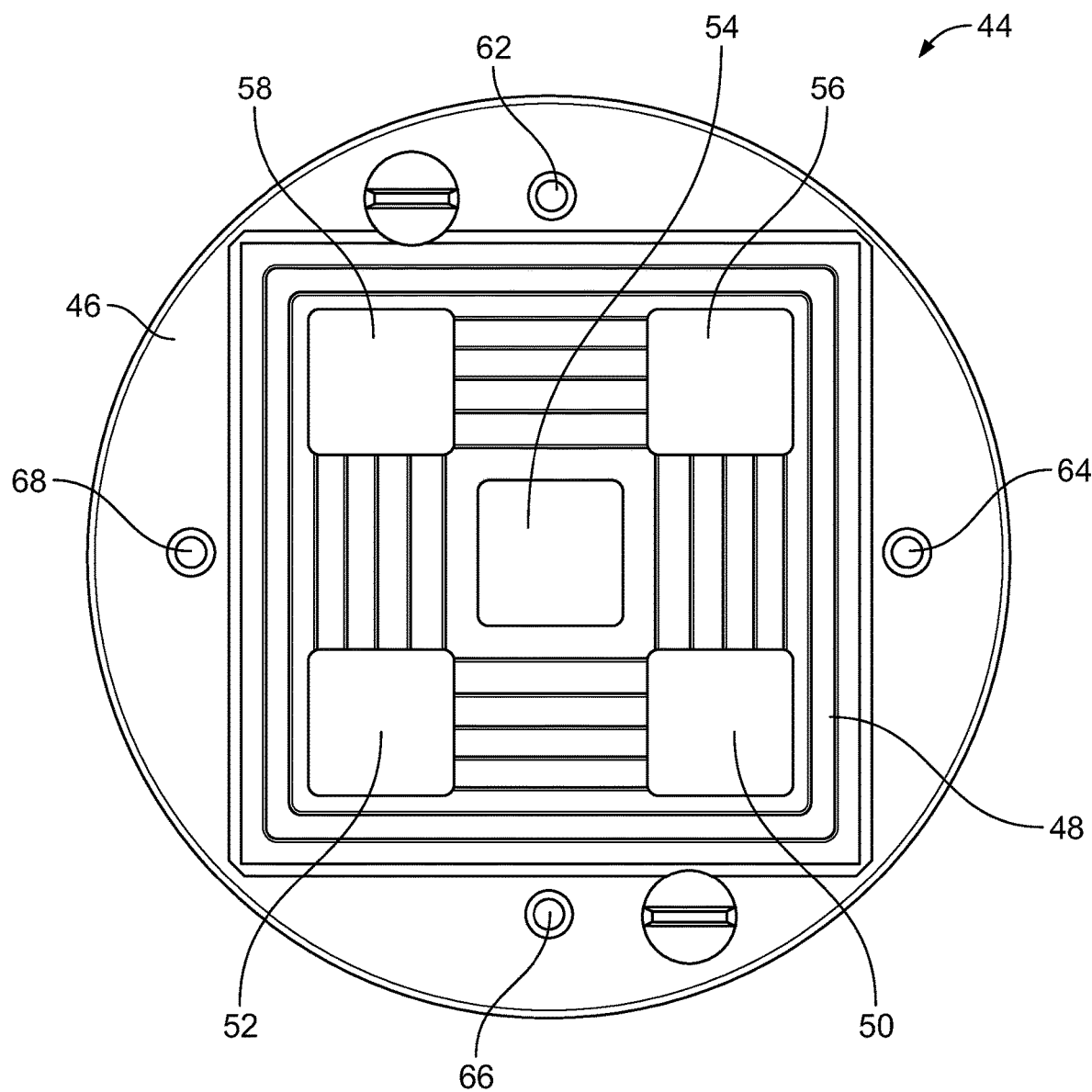
FIG. 5 is an end view of an embodiment of a dosimetry device of the present invention illustrating an embodiment of a photosensitivity matrix.

FIGS. 4 and 5 illustrate another embodiment of a dosimetry device 44. As shown, the dosimetry device 44 includes a housing 46 and a sensitivity matrix 48 that is comprised of a plurality of openings 50, 52, 54, 56, 58 formed therein. The matrix 48 is encapsulated by a UVB transparent optical window 60. In an embodiment, the matrix 48 can be a filter comprised of a single piece of glass, a plurality of different types of glass or crystalline materials. This filter can absorb varying percentages of a single incident dose of light, segment the energy into multiple beams or streams of energy of varying intensities and allow the various percentages of light to pass through and contact an individual's skin. To fix the device 52 to the laser delivery apparatus 10, in an embodiment, the device 44 includes a plurality of openings 62, 64, 66, 68 through which fasteners (not shown) can extend.

In an embodiment, the intensity of light that is able to pass through the openings 50, 52, 54, 56, 58 of the matrix 48 can range from approximately about 20% to 100%. In another embodiment, intensity of light that is able to pass through the openings 50, 52, 54, 56, 58 of the matrix 48 ranges from 20% to 90%. However, the number of openings, shape of the openings and intensity of light being permissible to pass through the openings of the matrix 48 can vary such that the number of openings can be greater or small than the numbers described herein.

In an embodiment, a single phototherapeutic dose of energy can be segmented directly into a plurality of beams of energy of different dosage levels using a filter arranged in a dosimetry device 12, 44. In another embodiment, two or more doses of energy are applied to an individual's skin through segmented filters arranged in a dosimetry device 12, 44 (e.g., a first dose test in a range of 100 to 500 mj/cm2 and a second dose test in a range of 600 to 1000 mj/cm2).

The device 12, 44 can be arranged in contact with an individual's body, the device 20, 44 can be releasably attached to an individual's body or the device 20, 44 can be arranged near an individual's body. The device 12, 44 can be reusable, disposable, and/or the sensitivity matrix 22, 54 can be replaced with a new or different matrix for each use or after a determined number of uses.

Figure 6:
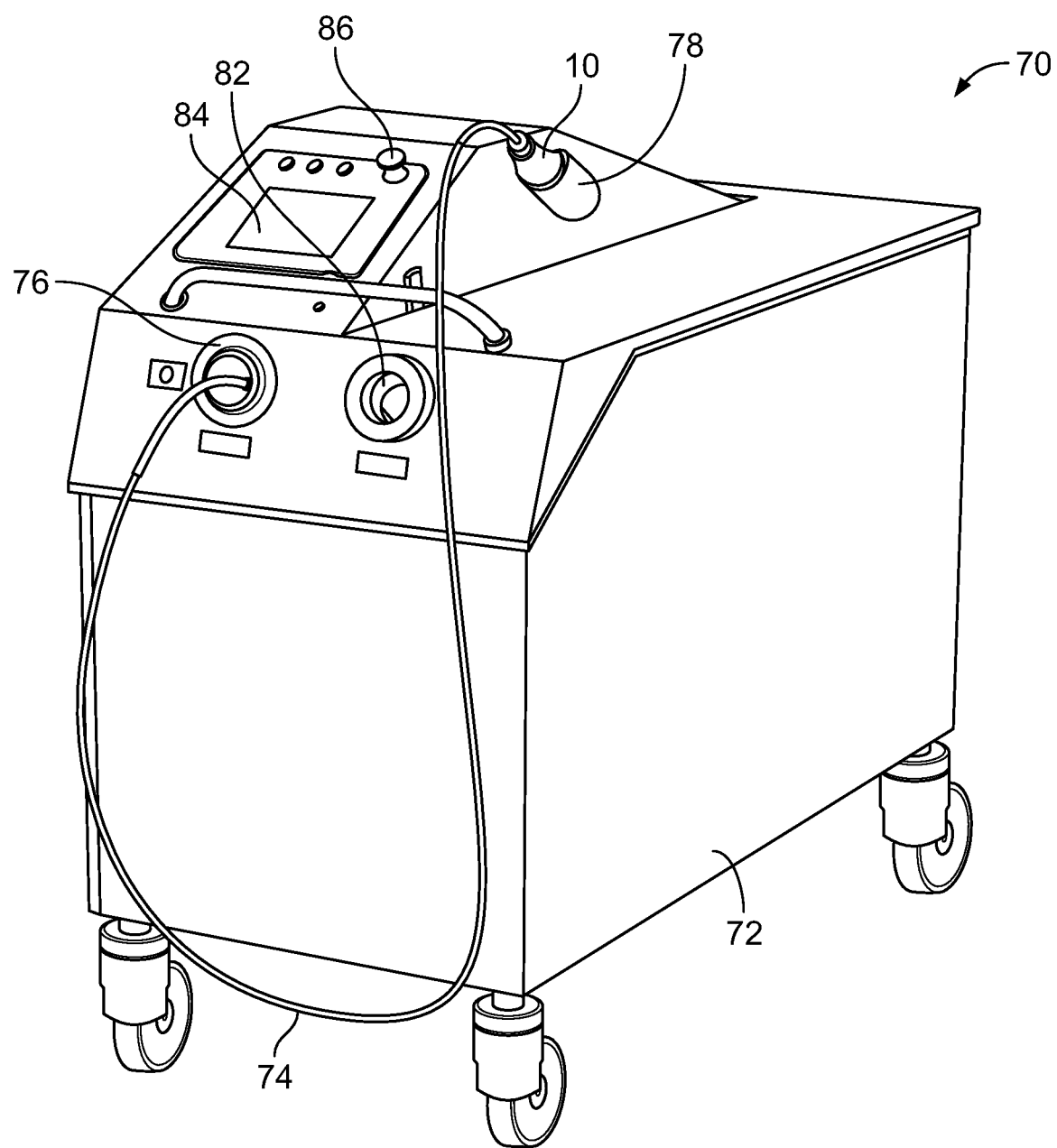
FIG. 6 is an embodiment of an excimer phototherapy system that is configured to delivery light energy through the photosensitivity matrix of a dosimetry device of the present invention.

FIG. 6 illustrates an embodiment of an excimer phototherapy system 70. The excimer phototherapy system 70 is designed to provide phototherapy for various dermatoses including psoriasis, vitiligo, leukoderma, atopic dermatitis, and alopecia by producing ultraviolet light energy within the UVB range (290-320 nm) of the electro-magnetic spectrum. Specifically, in an embodiment, the phototherapy system 70 is designed for treatment of various dermatoses in a narrow band, monochromatic wavelength at 308 nm for targeted phototherapy treatment, sparing healthy tissue from long-term cumulative UVB exposure. However, the delivery apparatus can distribute any form of energy in place of laser energy that is capable of treating various dermatoses.

The system 70 can be housed within and extend from a cart 72. The cart 72 includes a fiber-optic delivery cable 74 that is connected to the cart 72 at one end at a delivery port 76. The delivery apparatus, or hand piece, 10, which can rest in a hand piece cradle 78, is connected at the other end of the delivery cable 74. The hand piece 10, can include a user interface 80, which may be in the form of a pushbutton (See e.g., FIG. 1A) to control the delivery of energy (e.g., in the form of UVB light) from the system 70.

In order to perform a treatment session on an individual suffering from a skin condition, the hand piece 10 must first be calibrated. This can be done by placing the hand piece 10 in a calibration port 82 that extends into the cart 7. The cart 72 further includes, among other features, a control panel touch screen 84 for operation of the system 70 and an emergency stop switch 86.

Figure 7:
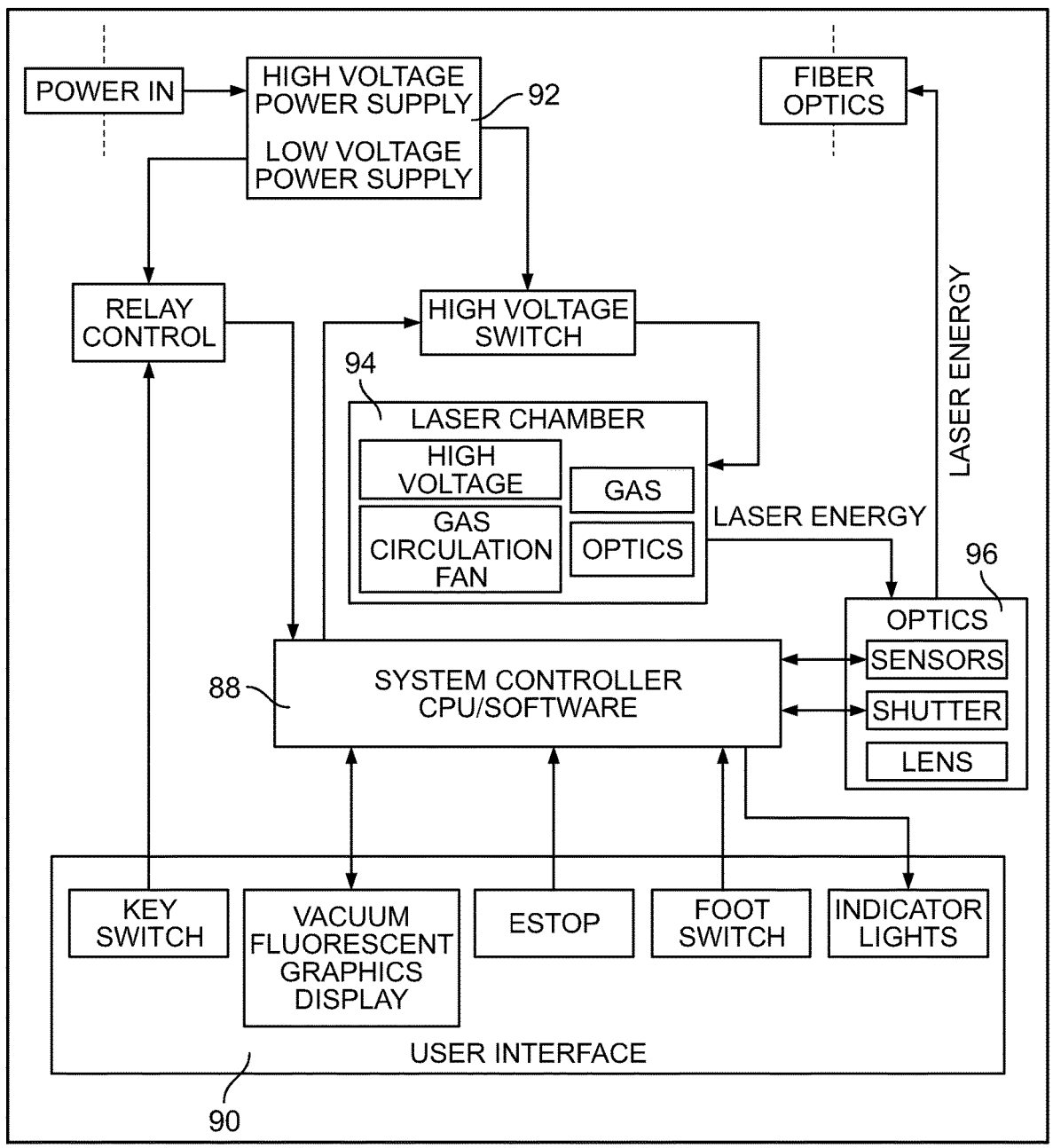
FIG. 7 is a schematic diagram depicting an embodiment of an excimer phototherapy system.

As shown schematically in an embodiment in FIG. 7, internal components of the excimer phototherapy system 70 can include a system controller (i.e., CPU/software) 88 that is capable of directly and/or indirectly interacting with a user interface 90, a power supply 92, a laser chamber 94 and optics components 96. Laser energy can be delivered from the system 70 by fiber optics to the hand piece 10 and onto an individual suffering from a skin condition.

In operation, upon determining a patient's MTD based on the results using the dosimetry device 12, 44, the total delivered dose, can be adjusted to optimize the effectiveness of the UVB dosing and minimize the number of required treatments and to ensure patient safety.

Figure 8:
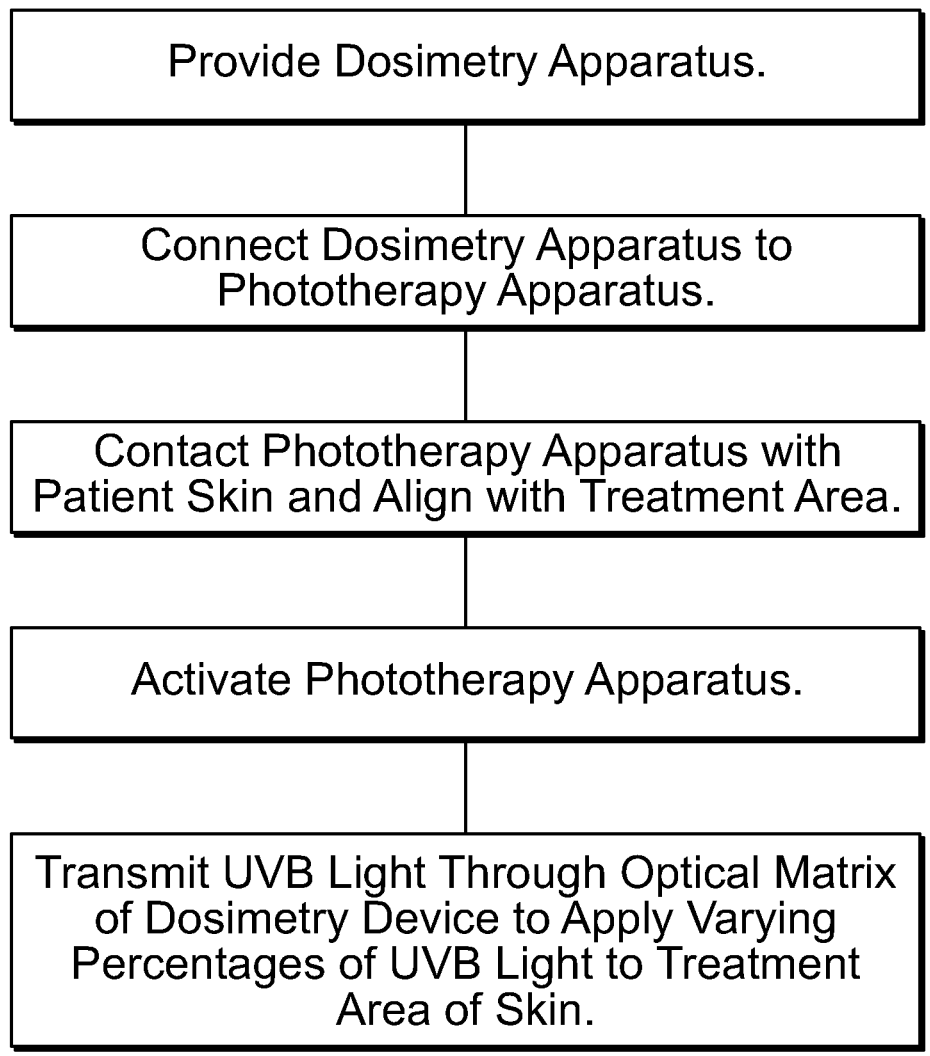
FIG. 8 is a flow chart outlining an embodiment of steps that can be taken to analyze a maximum tolerable dose of phototherapy that can be applied to a treatment area.

FIG. 8 illustrates a flow chart outlining an embodiment of steps that can be taken to analyze the MTD of phototherapy that can be applied to an individual suffering from a skin condition. As depicted in the flow chart, a dosimetry device can be provided that is then connected to the phototherapy apparatus. The phototherapy apparatus can then be placed near or in contact with a diseased region of an individual suffering from a skin condition. Once the device 12, 44 is orientated over a diseased region of skin, the delivery system 10 can then output a dose of UVB light that will travel through the matrix 20, 48 at varying intensities and contact a diseased region of skin at such varying intensities. Then, approximately 24 to 48 hours after applying the UVB dose of phototherapy to the diseased region of skin at varying intensities, the individual can then return to a clinician's office where the clinician can assess the tested area and determine the individual's MBD by observing which percentage(s) of the UVB light manifested a blistering response. By knowing the individual's MBD, the individual can subsequently be treated just below their MBD, at their optimal or MTD.

While reference has been made to specific embodiments described using specific terms, such description is for illustrative purposes only, and it is to be understood that modifications and variations to such embodiment, including, but not limited to, the substitution of equivalent features, materials, or parts, and the reversal of various features thereof, may be practiced by those of ordinary skill in the art without departing from the spirit and scope of the invention. As such, the drawings and the description are not to be taken as restrictive of the scope and are understood as broad and general teachings in accordance with the present invention.

What is claimed is:

1. A dosimetry device, comprising:
   a light delivery handpiece elongated along an axis between a proximal end and a distal end, a fiber optic cable extending from the proximal end of the handpiece to a remote source of narrow band, monochromatic UVB laser light with wavelength at 308 nm, and a beam shaping diaphragm between the proximal end and the distal end of the handpiece, the handpiece configured to emit from the distal end and along the axis a beam of UVB laser light provided through the fiber optic cable and output with a beam cross-section shaped by the beam shaping diaphragm, the beam cross-section defining a size of a treatment area;
   a housing releasably connected to the distal end of the handpiece along the axis;
   a two-dimensional optical matrix mounted in the housing and comprising a plurality of UVB light transmissive regions, each respective light transmissive region having a respective UVB transmittance percentage that is different from others of the plurality light transmissive regions,
   wherein the optical matrix is configured to receive the UVB light beam emitted from the distal end of the handpiece when the housing is releasably connected to the light delivery handpiece, and
   wherein, when a single dose of the UVB light beam at a predefined intensity is emitted from the handpiece and supplied to the optical matrix, the single dose of the UVB light beam is filtered by the optical matrix such that each respective light transmissive region emits a corresponding UVB light beam having a respective intensity different from the respective intensity of other light transmissive regions to simultaneously produce a plurality of regions of varying intensities UVB light, and
   wherein each of the light transmissive regions comprises at least one of UVB absorptive, reflective and partially transmissive material.

2. The dosimetry device of claim 1, wherein the intensity of light passing through the light transmissive regions ranges from about 20% of an intensity of the light that is supplied to the optical matrix in one region up to about 100% of the intensity of the light that is supplied to the optical matrix in another region.

3. The dosimetry device of claim 1, wherein the intensity of light passing through the light transmissive regions ranges from about 0% of an intensity of the light that is supplied to the optical matrix in one region up to about 90% of the intensity of the light that is supplied to the optical matrix in another region.

4. The dosimetry device of claim 1, wherein the matrix is substantially square.

5. The dosimetry device of claim 1, wherein each of the light transmissive regions include at least one of a metallic, multi-dielectric and a dielectric coating or volume absorbing materials in a UVB range.

6. The dosimetry device of claim 1, wherein the housing is circular.

7. The dosimetry device of claim 1, wherein the optical matrix is encapsulated by a UVB transparent optical window.

8. The dosimetry device of claim 1, wherein the beam shaping diaphragm is configured to output a light beam that is circular.

9. A method of treating an area of diseased skin of a patient, the method comprising the following steps:
   providing a light delivery system configured to emit from a distal end of a handpiece a beam of a selectable dose of UVB light along an output axis and at a wavelength of 308 nm, the light being emitted in a beam having a cross-section along the output axis defining a size of a treatment area of skin to which the beam can be applied, the selectable dose representing a total amount of UVB light energy per unit area provided by the beam, wherein the UVB light is UVB laser light, the handpiece is elongated along an axis between a proximal end and the distal end, a fiber optic cable extending from the proximal end of the handpiece to a remote source of the laser light;
   providing a dosimetry device comprising a housing having a two-dimensional optical matrix mounted therein and comprising a plurality of UVB light transmissive regions, each respective light transmissive region having a respective UVB transmittance percentage that is different from others of the plurality of light transmissive regions, the dosimetry device configured to be releasably connected to the distal end of the handpiece so that the optical matrix intersects a light beam emitted from the handpiece;
   connecting the dosimetry device to the distal end of the handpiece;
   placing the distal end of the handpiece with the dosimetry device connected thereto over a first region of the diseased skin so that the optical matrix arranged therein is facing the first region of the diseased skin;
   initiating a single first dose of the UVB light from the remote source of the laser light,
   wherein the first dose of the UVB light is emitted from the handpiece to intersect the optical matrix, each respective light transmissive region in the optical matrix operating to produce a respective dose of the UVB light within a corresponding respective sub-region in the first region of the diseased skin, the respective dose being a function of the first dose and UVB transmittance percentage of the respective light transmissive region, wherein all of the respective doses of the UVB light are simultaneously delivered to the first region of the diseased skin;

subsequent to applying the first dose of the UVB light as modified by the optical matrix to the first region of the diseased skin, examining the respective sub-regions in the first region of the diseased skin to identify blistered diseased skin and determine a minimum blistering dose (MBD) for the first region of the diseased skin based on a position of blistered diseased skin within the first region of the diseased skin and characteristics of the light transmissive regions in the optical matrix, the MBD being less than or equal to the first dose;

determining as a maximum tolerable dose (MID) of UVB light that can be applied to the diseased skin without blistering, a dose value that is less than the determined MBD, removing the dosimetry device from the distal end of the handpiece;

placing the distal end of the handpiece without the dosimetry over the diseased skin; and applying the MTD of the UVB light to the diseased skin.

10. The method of claim 9, wherein the transmittance percentages of the light transmissive regions of the optical matrix range from about 20% in one region up to about 100% in another region.

11. The method of claim 9, wherein the transmittance percentages of the light transmissive regions of the optical matrix range from about 0% in one region up to about 90% in another region.

12. The method of claim 9, wherein the step of examining the respective sub-regions in the first region of the diseased skin to identify blistered diseased skin and determine the MBD is carried out approximately 24 to 48 hours after applying the first dose of the UVB light as modified by the optical matrix to the first region of the diseased skin.

13. The method of claim 9, wherein the optical matrix is encapsulated by a UVB transparent optical window.

* * * * *